US010575935B2

(12) United States Patent
Wei et al.

(10) Patent No.: US 10,575,935 B2
(45) Date of Patent: Mar. 3, 2020

(54) IMPLANTABLE URINARY TRACT VALVE

(71) Applicant: Medtronic, Inc., Minneapolis, MN (US)

(72) Inventors: Xuan K. Wei, Minnetonka, MN (US); Eric H. Bonde, Minnetonka, MN (US); Charles Thomas Bombeck, Lino Lakes, MN (US)

(73) Assignee: Medtronic, Inc., Minneapolis, MN (US)

(*) Notice: Subject to any disclaimer, the term of this patent is extended or adjusted under 35 U.S.C. 154(b) by 227 days.

(21) Appl. No.: 15/707,472

(22) Filed: Sep. 18, 2017

(65) Prior Publication Data
US 2018/0000576 A1    Jan. 4, 2018

Related U.S. Application Data

(63) Continuation of application No. 14/495,002, filed on Sep. 24, 2014, now Pat. No. 9,763,762.

(Continued)

(51) Int. Cl.
*A61F 2/00* (2006.01)

(52) U.S. Cl.
CPC .......... *A61F 2/0027* (2013.01); *A61F 2/0018* (2013.01); *A61F 2/0022* (2013.01)

(58) Field of Classification Search
CPC ..... A61F 2/0018; A61F 2/0027; A61F 2/0022
See application file for complete search history.

(56) References Cited

U.S. PATENT DOCUMENTS

| 3,731,670 A | 5/1973 | Loe |
| 3,768,102 A | 10/1973 | Kwan-Gett et al. |

(Continued)

FOREIGN PATENT DOCUMENTS

| DE | 2537506 A1 | 3/1977 |
| EP | 0193406 B1 | 2/1991 |

(Continued)

OTHER PUBLICATIONS

Examination Report from counterpart European Application No. 14784161.3, dated Oct. 8, 2018, 6 pp.

(Continued)

*Primary Examiner* — Christine H Matthews
*Assistant Examiner* — Joshua Daryl D Lannu
(74) *Attorney, Agent, or Firm* — Shumaker & Sieffert, P.A.

(57) ABSTRACT

A urinary tract valve includes an expandable valve element positionable within a bladder of a patient via a urinary tract of the patient in a collapsed configuration. The expandable valve element is configured to transition from the collapsed configuration to an expanded configuration after being positioned within the bladder of the patient. The expandable valve element includes a ferromagnetic element that facilitates selective control of the expandable valve element with a magnetic field between an open position and a closed position when positioned within the bladder of the patient. In the closed position, the expandable valve element is configured to seal an internal urethral opening of the patient. In the open position, the expandable valve element is configured to allow urine to pass from the bladder of the patient, through an internal urethral opening of the patient and into a urethra of the patient.

20 Claims, 12 Drawing Sheets

Related U.S. Application Data

(60) Provisional application No. 61/882,338, filed on Sep. 25, 2013.

(56) References Cited

U.S. PATENT DOCUMENTS

| | | | |
|---|---|---|---|
| 3,812,841 | A | 5/1974 | Isaacson |
| 3,958,556 | A | 5/1976 | Schenk |
| 4,154,226 | A | 5/1979 | Hennig et al. |
| 4,209,010 | A | 6/1980 | Ward et al. |
| 4,679,546 | A | 7/1987 | van Waalwijk van Doorn et al. |
| 4,865,588 | A | 9/1989 | Flinchbaugh |
| 4,994,019 | A | 2/1991 | Fernandez et al. |
| 5,004,454 | A | 4/1991 | Beyar et al. |
| 5,030,199 | A | 7/1991 | Barwick et al. |
| 5,041,092 | A | 8/1991 | Barwick |
| 5,140,999 | A | 8/1992 | Ardito |
| 5,366,506 | A | 11/1994 | Davis |
| 5,624,395 | A | 4/1997 | Mikhail et al. |
| 5,711,314 | A | 1/1998 | Ardito |
| 5,782,916 | A | 7/1998 | Pintauro et al. |
| 5,906,575 | A | 5/1999 | Conway et al. |
| 5,997,467 | A | 12/1999 | Connolly |
| 6,066,088 | A | 5/2000 | Davis |
| 6,132,365 | A | 10/2000 | Sigurdsson |
| 6,171,231 | B1 | 1/2001 | Connolly |
| 6,540,665 | B1 | 4/2003 | Connolly |
| 6,589,228 | B2 | 7/2003 | Holzer |
| 6,673,051 | B2 | 1/2004 | Flinchbaugh |
| 6,855,126 | B2 | 2/2005 | Flinchbaugh |
| 7,223,228 | B2 | 5/2007 | Timm et al. |
| 7,803,106 | B2 * | 9/2010 | Whalen .................. A61F 2/0018 600/30 |
| 8,190,262 | B2 | 5/2012 | Gerber et al. |
| 9,763,762 | B2 | 9/2017 | Wei et al. |
| 2002/0151923 | A1 | 10/2002 | Holzer |
| 2002/0165427 | A1 * | 11/2002 | Yachia .................. A61F 2/0022 600/31 |
| 2003/0229264 | A1 | 12/2003 | Connors et al. |
| 2004/0138520 | A1 | 7/2004 | Connors et al. |
| 2005/0267324 | A1 | 12/2005 | Timm et al. |
| 2006/0155163 | A1 | 7/2006 | Yachia et al. |
| 2007/0276342 | A1 | 11/2007 | Lin et al. |
| 2010/0241241 | A1 | 9/2010 | McKnight et al. |
| 2012/0184980 | A1 | 7/2012 | Anderson et al. |
| 2012/0239006 | A1 | 9/2012 | Wijay et al. |
| 2013/0072998 | A1 | 3/2013 | Su et al. |
| 2013/0079841 | A1 | 3/2013 | Su et al. |

FOREIGN PATENT DOCUMENTS

| | | |
|---|---|---|
| EP | 1072238 B1 | 11/2003 |
| WO | 0054702 A1 | 9/2000 |

OTHER PUBLICATIONS

"Urinary Incontinence," MayoClinic.com, http://www.mayoclinic.com/health/urinaryincontinence/DS00404/DSECTION=8, Apr. 28, 2006, 5 pp.

International Search Report and Written Opinion from International Patent Application No. PCT/US2014/057196, dated Dec. 16, 2014, 12 pp.

International Preliminary Report on Patentability from International Application No. PCT/US2014-057196, dated Apr. 1, 2016, 8 pp.

Prosecution History from U.S. Appl. No. 14/495,002, from Aug. 16, 25, 2016 through May 19, 2017, 50 pp.

* cited by examiner

IMPLANTABLE URINARY TRACT VALVE

This application is a continuation of U.S. patent application Ser. No. 14/495,002 filed Sep. 24, 2014, which claims the benefit of U.S. Provisional Application No. 61/882,338, filed on Sep. 25, 2013, the entire contents of each of these applications are incorporated by reference herein.

TECHNICAL FIELD

The disclosure relates to medical devices implantable in and near the urinary tract.

BACKGROUND

Urinary incontinence is the loss of voluntary control to retain urine. Urinary incontinence may be the result of a number of causes, such as old age, disease, pregnancy or trauma, or no apparent cause, as is the case with urge incontinence. Some patients may experience urinary incontinence during stressful events, such as sneezing, laughing, coughing, lifting, or other activity that puts pressure on the bladder.

Some patients suffering from urinary incontinence may deal with the condition by conservative measures, such as performing exercises to strengthen the outer urethral sphincter. For some patients, however, such conservative measures are ineffective. In a healthy human being, the internal and external urethral sphincters contract to prevent the escape of urine, the external sphincter being under the voluntary control of the patient. In some patients, however, the patient may have some control over the external sphincter, but one or both sphincters lack the ability to maintain closure of the urethra and prevent the escape of urine.

SUMMARY

This disclosure relates to devices, systems, and methods for facilitating the selective excretion of urine from a patient's bladder. In some examples, an implantable medical device includes a valve including an expandable valve element configured to transition from a collapsed configuration to an expanded configuration after being positioned within a bladder of a patient. The valve element is configured to be moved relative to an internal urethral opening of the patient, e.g., using a magnet located outside of the patient and a ferromagnetic element of the valve element, to selectively control the valve element to seal the internal urethral opening of the patient (referred to herein as a "closed position" of the valve element) or to allow urine to pass from the bladder of the patient (referred to herein as an "open position" of the valve element). Different disclosed examples may be used to control urinary incontinence and/or urinary retention.

In one example, this disclosure is directed to a device comprising an expandable valve element configured to be positioned within a bladder of a patient via a urinary tract of the patient when the expandable valve element is in a collapsed configuration. The expandable valve element is configured to transition from the collapsed configuration to an expanded configuration after being positioned within the bladder of the patient via the urinary tract of the patient. The expandable valve element includes a ferromagnetic element that facilitates selective control of the expandable valve element with a magnetic field between an open position and a closed position when positioned within the bladder of the patient. In the closed position and in the expanded configuration, the expandable valve element is configured to seal an internal urethral opening of the patient. In the open position, the expandable valve element is configured to allow urine to pass from the bladder of the patient, through an internal urethral opening of the patient and into a urethra of the patient.

In another example, this disclosure is directed to a system comprising an external magnet configured to produce a magnetic field and an implantable device. The implantable device includes an expandable valve element configured to be positioned within a bladder of a patient via a urinary tract of the patient when the expandable valve element is in a collapsed configuration. The expandable valve element is configured to transition from the collapsed configuration to an expanded configuration after being positioned within the bladder of the patient via the urinary tract of the patient. The expandable valve element includes a ferromagnetic element that facilitates selective control of the expandable valve element with the magnetic field between an open position and a closed position when positioned within the bladder of the patient. In the closed position and in the expanded configuration, the expandable valve element is configured to seal an internal urethral opening of the patient. In the open position, the expandable valve element is configured to allow urine to pass from the bladder of the patient, through an internal urethral opening of the patient and into a urethra of the patient.

In further example, this disclosure is directed to a method comprising inputting a control signal to vacate urine from a user's bladder via a programmer of a urinary tract valve system. The urinary tract valve system comprises the programmer, a wearable magnet device that includes an electromagnet, and an implantable device. The implantable device includes an expandable valve element configured to be positioned within a bladder of a patient via a urinary tract of the patient when the expandable valve element is in a collapsed configuration. The expandable valve element is configured to transition from the collapsed configuration to an expanded configuration after being positioned within the bladder of the patient via the urinary tract of the patient. The expandable valve element includes a ferromagnetic element that facilitates selective control of the expandable valve element with the magnetic field between an open position and a closed position when positioned within the bladder of the patient. In the closed position and in the expanded configuration, the expandable valve element is configured to seal an internal urethral opening of the patient. In the open position, the expandable valve element is configured to allow urine to pass from the bladder of the patient, through an internal urethral opening of the patient and into a urethra of the patient.

The details of one or more examples of this disclosure are set forth in the accompanying drawings and the description below. Other features, objects, and advantages of this disclosure will be apparent from the description and drawings, and from the claims.

DETAILED DESCRIPTION

Figure 1A:
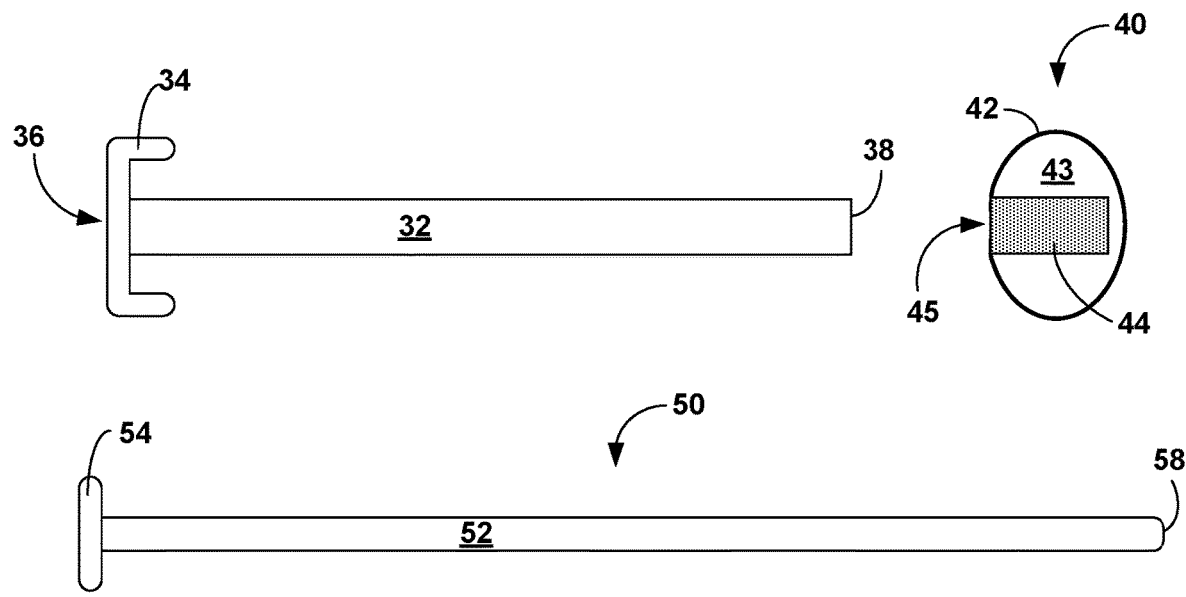
FIGS. 1A-1C illustrate an example system including an insertion catheter and an ellipsoid-shaped expandable valve element configured to be positioned within a bladder of a patient to facilitate selective excretion of urine from the patient's bladder.
Figure 1B:
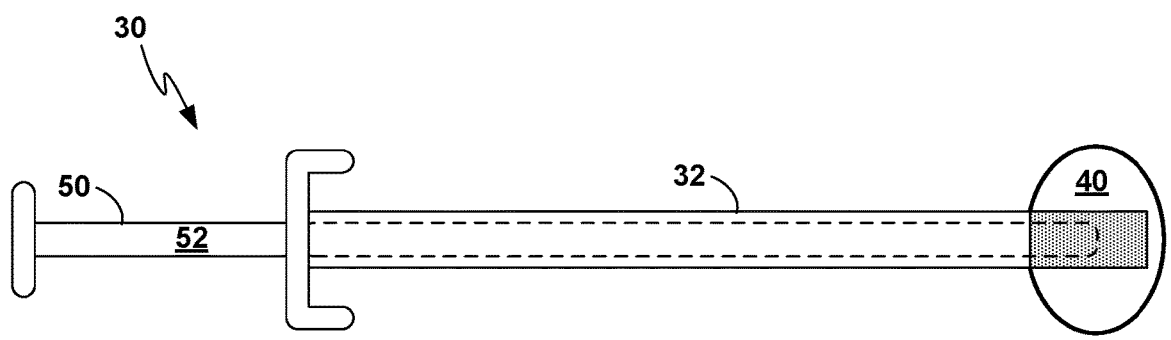
Figure 1C:
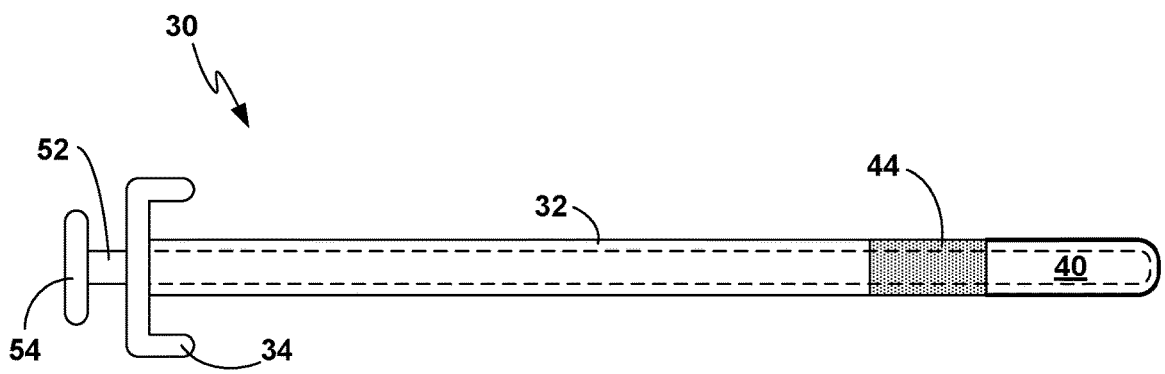

FIGS. 1A-1C illustrate an example system 30 including ellipsoid-shaped expandable valve element 40. Expandable valve element 40 is positionable within a bladder of a patient to facilitate selective excretion of urine from the patient's bladder. The system further includes insertion catheter 32 and insertion rod 50. Insertion catheter 32 and insertion rod 50 combine to facilitate insertion of ellipsoid-shaped expandable valve element 40 within a bladder of a patient via a urinary tract of the patient when expandable valve element 40 is in a collapsed configuration, as shown in FIG. 1C. Insertion catheter 32 and insertion rod 50 may also facilitate retrieval of expandable valve element 40 from the bladder and/or urethra of the patient.

Expandable valve element 40 is configured to assume an expanded configuration, as shown in FIG. 1B, to facilitate selective excretion of urine from a patient's bladder when positioned within the patient's bladder. Expandable valve element 40 is configured to assume a collapsed configuration, as shown in FIG. 1C, to facilitate implantation of element 40 in the patient's bladder through the patient's urethra. Expandable valve element 40 is configured to transition from the collapsed configuration to the expanded configuration after being positioned within the bladder of the patient via the urinary tract of the patient.

Expandable valve element 40 includes elastomeric outer element 42 and internal element 44 configured to facilitate the transition from the collapsed configuration to the expanded configuration. In particular, in the example shown in FIGS. 1A-1C, internal element 44 forms through-hole 45. One end of through-hole 45 is open and configured to receive distal end 58 of insertion rod 50. The other end of through-hole 45 is adjacent to an internal surface of elastomeric outer element 42 such that extension of insertion rod 50 within insertion catheter 32 results in the stretching of elastomeric outer element 42 while internal element 44 is held by insertion catheter 32. For example, internal element 44 may be held by way of a mechanical connection, such as a tether or clamp to insertion catheter 32 or by a magnetic connection to distal end 38 of insertion catheter 32. Elastomeric outer element 42 may be formed from a soft polymer, such as silicone as a thin membrane configured to conform to the bladder wall in the trigone area.

Expandable valve element 40 is configured to assume the collapsed position when internal element 44 is securely held by insertion catheter 32 and insertion rod 50 is extended through through-hole 45 and distal end 58 of insertion rod 50 pressed against the internal surface of the elastomeric element 42 to stretch elastomeric outer element 42 such that elastomeric outer element 42 assumes an elongated shape, as shown in FIG. 1C. Internal element 44 may be relatively rigid as compared to elastomeric outer element 42. In some examples, the proximal end of insertion catheter 32 may include a locking mechanism configured to secure the position of insertion rod 50 relative to insertion catheter 32 in order to maintain the stretched elongated shape of elastomeric outer element 42 during an insertion procedure.

When expandable valve element 40 is in the expanded configuration, elastomeric outer element 42 assumes a shape configured to facilitate sealing of the internal urethral opening of the patient. Expandable valve element 40 can be configured to be moved into position to seal the internal urethral opening of the patient by a magnet, which may be carried external to the patient. For example, a patient (or patient caretaker) can pull a ferromagnetic element of expandable valve element 40 toward the internal urethral opening of the patient with the magnetic field generated by the magnet. In some examples, internal element 44 may include the ferromagnetic element of expandable valve element 40. When selectively controlled using the magnetic field to assume an open position relative to the internal urethral opening, the expandable valve element is configured to allow urine to pass from the bladder of the patient, through the internal urethral opening of the patient and into the urethra of the patient.

In some examples, elastomeric outer element 42 is configured to assume an about ellipsoid shape when in the expanded configuration. In the same or different examples, elastomeric outer element 42 is configured to assume the shape configured to facilitate sealing of the internal urethral opening of the patient while in a substantially relaxed state, such as that shown in FIG. 1A. As referred to herein, a relaxed state represents the state at which an element is not under significant elastic deformation.

In other examples, elastomeric outer element 42 may be inflated with a biocompatible substance after insertion into the bladder of a patient. In such examples, insertion rod 50 may include an aperture configured to permit passage of the substance into elastomeric outer element 42 to inflate element 42. Any suitable combination of liquid and/or gaseous fluids may be used to inflation of elastomeric outer element 42. In some examples, the composition and/or amount inflation fluid may be selected to provide a desired buoyancy for expandable valve element 40, such as an approximately neutral buoyancy within the bladder of a patient. In this case, when expandable valve element 40 is released from an external magnetic field, expandable valve element 40 would be free floating in the urine versus pushing on the dome of the bladder. This may provide improved patient comfort as compared to an example in which expandable valve element 40 is less dense than urine within the bladder of the patient.

As previously mentioned, insertion catheter 32 is configured to facilitate the implantation of the expandable valve element 40 in the collapsed configuration via the urinary tract of the patient and the remote deployment of expandable valve element 40 within the bladder of the patient. Insertion catheter 32 includes an elongated tube section forming through-hole 36, which extends from a proximal end of insertion catheter 32 and adjacent grip 34 through distal end 38 of insertion catheter 32. Grip 34 facilitates hand-held manipulation (e.g., by a clinician) of insertion catheter 32 during an insertion or retrieval procedure. Insertion rod 50 includes an elongated body element 52, which is configured to fit within through-hole 36 of insertion catheter 32. Insertion rod 50 includes grip 54 configured to facilitate hand-held manipulation (e.g., by a clinician) of insertion rod 50 during an insertion or retrieval procedure. Insertion rod 50 is longer than insertion catheter 32 such that the distal end 58 of insertion rod 50 may protrude from the distal end 38 of insertion catheter 32 when elongated body element 52 of insertion rod 50 is positioned within through-hole 36 of insertion catheter 32 such that grip 54 abuts grip 34.

Insertion catheter 32 and insertion rod 50 may be formed from materials providing sufficient rigidity to facilitate insertion of expandable valve element 40 into a patient's urethra. For example, insertion catheter 32 may be formed from a polymeric material, or a metallic material, such as a stainless steel material, a combination thereof or another suitable material. Similarly, insertion rod 50 may be formed from a polymeric material, or a metallic material, such as a stainless steel material, a combination thereof or another suitable material.

In an example, insertion catheter 32 also facilitates removal of expandable valve element 40 from the bladder of a patient. In one example, a continuity check may be performed between expandable valve element 40 and distal end 38 of insertion catheter 32 to indicate when catheter 32 is properly connected and aligned with expandable valve element 40 prior to deflation and removal of expandable valve element 40 from the bladder of a patient. For example, corresponding electrical contacts on expandable valve element 40 and on distal end 38 of insertion catheter 32 may facilitate the continuity check. In one example, a light, such as a light emitting diode (LED) on the insertion catheter 32 lights up when the electrical continuity is below a certain threshold to indicate that distal end 38 of insertion catheter 32 is properly connected and aligned with expandable valve element 40. This would allow a user (e.g., the patient or a clinician) the confidence to deflate expandable valve element 40 using a needle inserted via through-hole 36 of insertion catheter 32, for example, without fear of perforating their bladder or urethra. When expandable valve element 40 is deflated, expandable valve element 40 assumes the collapsed configuration.

In another example, through-hole 36 of insertion catheter 32 may be used to deploy a hook instead of a needle in order to secure expandable valve element 40 for removal from the bladder of a patient. When expandable valve element 40 is properly connected (e.g., using the electrical contacts described above) and aligned with distal end 38 of insertion catheter 32, the hook may be deployed via through-hole 36 of insertion catheter 32 and rotated into place to grasps a corresponding notch or handle (not shown) on expandable valve element 40. The notch or handle may be used to mechanically pull open a valve (not shown) within internal element 44 by which expandable valve element 40 can be inflated or deflated. When the pull force is released and the hook is rotated to release the notch or handle, the valve within internal element 44 can returns to its normally closed state.

In another example, through-hole 36 of insertion catheter 32 may be used to deploy a star-driver or similar screwdriver-like head. When expandable valve element 40 is properly connected and aligned with distal end 38 of insertion catheter 32, the screwdriver-like head may be deployed via through-hole 36 of insertion catheter 32 and advanced into place where it mates with a screw-like valve in internal element 44 of expandable valve element 40. The screwdriver-like head may be rotated counter clockwise to open the valve by which expandable valve element 40 can be inflated or deflated. To close the valve, the screwdriver-like head may be rotated in a clockwise direction.

As these examples illustrate, a variety of techniques may be used to inflate and deflate expandable valve element 40 in examples in which expandable valve element 40 is filled with an inflation media to transition between the collapsed configuration and the expanded configuration. Other examples are also possible.

When expandable valve element 40 is in an expanded state, expandable valve element 40 is configured to be moved between an open position and a closed position. In the closed position, expandable valve element 40 is configured to seal an internal urethral opening of the patient. In the open position, expandable valve element 40 is configured to allow urine to pass from the bladder of the patient, through the internal urethral opening of the patient and into the urethra of the patient.

Figure 2:
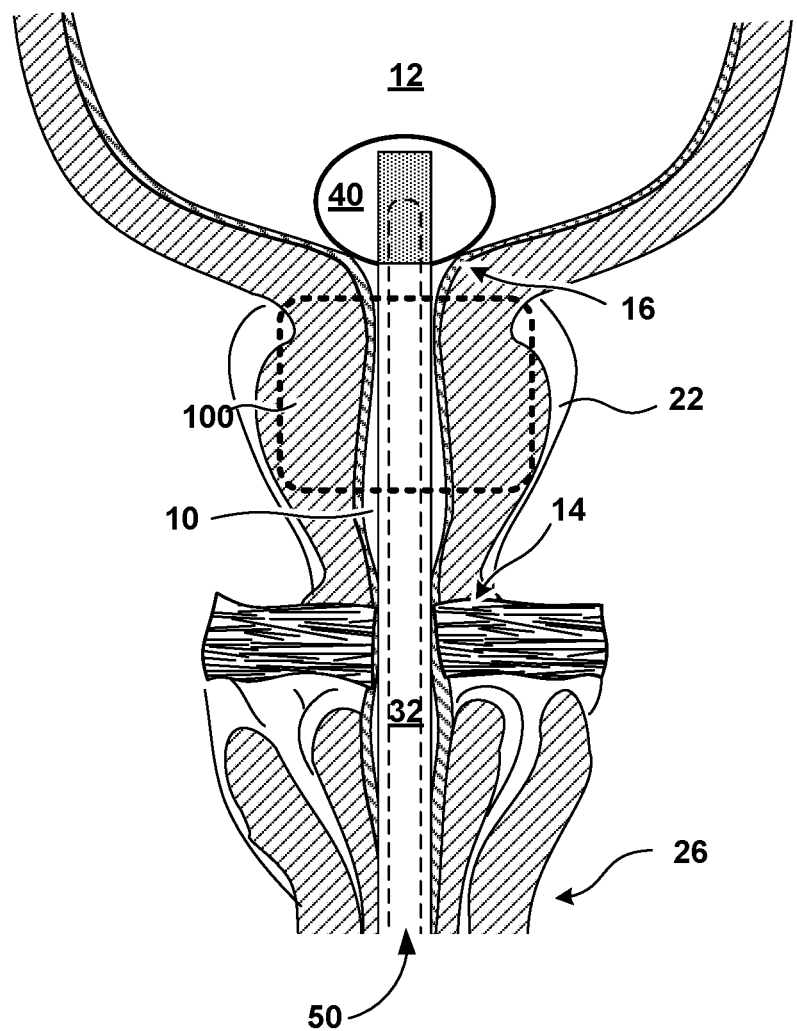
FIG. 2 illustrates the ellipsoid-shaped expandable valve element of FIGS. 1A-1C positioned within a bladder of a patient after insertion through the patient's urethra with the insertion catheter of FIGS. 1A-1C.

In the example shown in FIGS. 1A-1C, expandable valve element 40 includes a ferromagnetic element, which may be included in internal element 44, that facilitates selective control of expandable valve element 40 to move element 40 between the closed position and the open position. As discussed in further detail below, the ferromagnetic element is configured to interact with a magnet, e.g., located outside the patient when the expandable valve element 40 is in the expanded configuration and positioned within the bladder of the patient. As illustrated in FIG. 2, when selectively controlled using the magnetic field to assume a closed position, expandable valve element 40 is configured to seal an internal urethral opening of the patient.

FIG. 2 represents a coronal cross section of anatomical structures surrounding urethra 10 of a male patient. FIG. 2 illustrates expandable valve element 40 in the expanded configuration and positioned within bladder 12 of a patient after insertion through urethra 10 with insertion catheter 32. Urethra 10 is a tube, including a wall and a lumen that extends from the urinary bladder 12 to an external urethral orifice (not shown in FIG. 2). In a patient without urinary incontinence, flow of urine from bladder 12 and through urethra 10 is naturally controlled by an internal urinary sphincter 16 and an external urinary sphincter 14. Internal urinary sphincter 16 may not be considered to be a separate muscle, but, rather, is a portion of bladder 12 that operates as a sphincter. Internal urinary sphincter 16 is not under voluntary control of the patient.

External urinary sphincter 14 is further away from bladder 12 than internal urinary sphincter 16. External urinary sphincter 14 encircles urethra 10 and is reinforced by the pelvic diaphragm. Contraction and relaxation of external urinary sphincter 14 is under the voluntary control of the patient.

These properties of the external urinary sphincter are true in females as well as in males, but in males, the prostate encircling urethra 10 is interposed between bladder 12 the pelvic diaphragm. In addition, a male's urethra is typically much longer than a female's urethra, because the urethra of a male traverses the penis 26.

In patients experiencing urinary incontinence, internal urinary sphincter 16 and/or external urinary sphincter 14 may no longer restrict the flow of urine from bladder 12 through urethra 10 in an effective manner.

As shown in FIG. 2, expandable valve element 40 is positioned within bladder 12 to control the flow of urine from bladder 12 into urethra 10. FIG. 2 further illustrates insertion catheter 32 and insertion rod 50 within urethra 10 following the insertion of expandable valve element 40 into bladder 12 via urethra 10.

In order to deliver expandable valve element 40 to bladder 12 via urethra 10, expandable valve element 40 is secured to distal end 38 of insertion catheter 32. Expandable valve element 40 is set into a collapsed configuration, such as by stretching of elastomeric outer element 42 using insertion rod 50 and/or providing expandable valve element 40 in a deflated state, that is, without an inflation fluid, as discussed with respect to FIGS. 1A-1C.

While secured to distal end 38 of insertion catheter 32, expandable valve element 40 is inserted into the end of urethra 10 and pushed through urethra 10 with insertion catheter 32 until reaching bladder 12. Once expandable valve element 40 reaches bladder 12, expandable valve element 40 can assume its expanded configuration. In one example, insertion rod 50 may be retracted to allow expandable valve element 40 to assume an approximately ellipsoid shape. In another example, an inflation fluid may be injected into expandable valve element 40. Once in the expanded configuration, expandable valve element 40 may block the urethra at the trigone area to prevent the discharge of urine within bladder into urethra 10.

Expandable valve element 40 includes a ferromagnetic material configured to facilitate manipulation of element 40 from a position external to the patient. In one example, magnetic device 100 may be worn in undergarments or outside of the pelvic floor, where magnetic device 100 is configured to produce electromagnetic force when needed to pull expandable valve element 40 into position to seal the bladder neck, e.g., to prevent urine leak and/or repel expandable valve element 40 to release the temporary blockage of the bladder neck.

In one example, magnetic device 100 may be an electromagnetic device. When the patient experiences an urge sensation, the patient can activate the electromagnetic device; after being activated, electromagnetic device generates a magnetic field that generates Lorentz force that pulls expandable valve element 40 toward the bladder neck. Once expandable valve element 40 moves to the bladder neck, expandable valve element 40 blocks urine leakage from the bladder. When the urge sensation subsides or when it is socially acceptable to void, the patient can deactivate the magnetic field and/or activate an external magnet device to generate a magnetic field that generates Lorentz force in the direction that repels expandable valve element 40 to move element 40 away from the bladder neck and permit passage of urine through the bladder neck.

Magnetic device 100 may contain battery, circuit, and one or more telecommunication modules. In some examples, magnetic device 100 may receive control instructions wirelessly from a separate activator. The activator can be in any suitable form, such as in the form of a wristwatch, bracelet, keyboard or mobile hand-held device. While in some examples, magnetic device 100 may contain a permanent magnet with a persistent magnetic field, incorporating a dynamic magnetic field may allow expandable valve element 40 to be free floating most of the time and only pulled down toward the bladder neck when needed to block leakage. This may provide improved patient comfort and reduce bladder neck stress as compared to a system in which expandable valve element 40 remains positioned within the bladder neck.

In case of stress incontinence, expandable valve element 40 can be activated when the patient is physically active or desires protection against stress situations such as laughing, coughing, and the like. In another example, the activation and deactivation of the magnetic field can be triggered automatically by communication from sensors such as accelerometer and pressure sensors within expandable valve element 40, magnetic device 100, the activator or elsewhere.

Magnetic device 100 may have telecommunication capability to transmit data on activation and deactivation time marker and duration. In one example, the data can be transmitted to the activator or another external mobile device to trend compliance, utilization, and symptom change.

Expandable valve element 40 may remain within bladder 12 for a prescribed period of time before being removed. When removal is needed, insertion catheter 32 can be inserted into urethra 10. In some examples, insertion catheter 32 may generate either a permanent or activated magnetic field to attract expandable valve element 40 toward distal end 38 of insertion catheter 32. Expandable valve element 40 may is be collapsed to assume the collapsed configuration, such as by deflation or stretching using insertion rod 50 or otherwise. Once expandable valve element 40 is in the collapsed configuration, it may be extracted from the bladder via urethra 10. In some examples, expandable valve element 40 may be retracted into through-hole 36 of insertion catheter 32 in the collapsed configuration prior to its extraction via urethra 10.

Figure 3A:
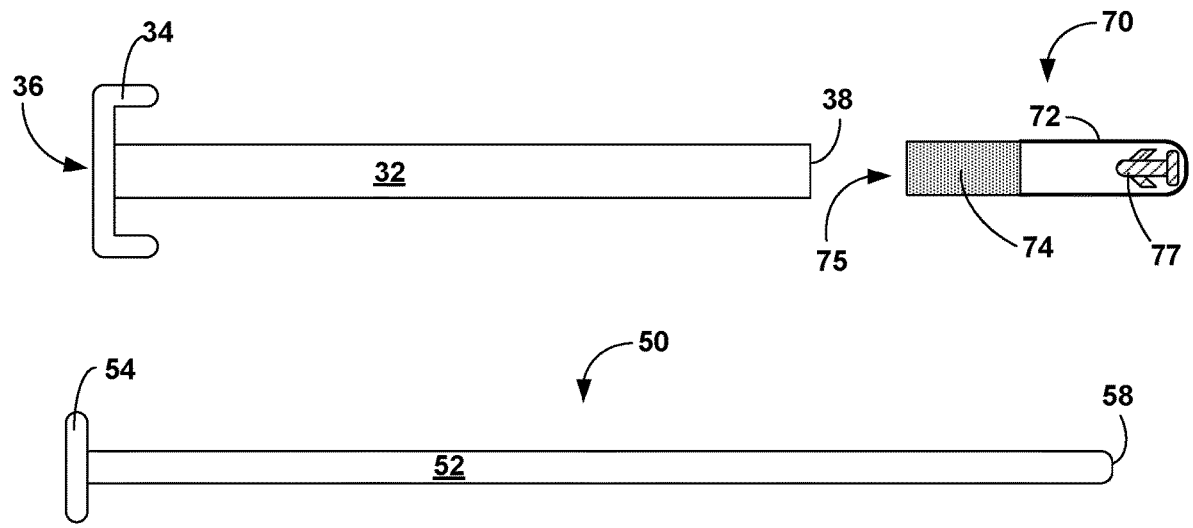
FIGS. 3A-3C illustrate an example system including an insertion catheter and an expandable valve element including snap-lock features, the expandable valve element being positionable within a bladder of a patient to facilitate selective excretion of urine from the patient's bladder.
Figure 3B:
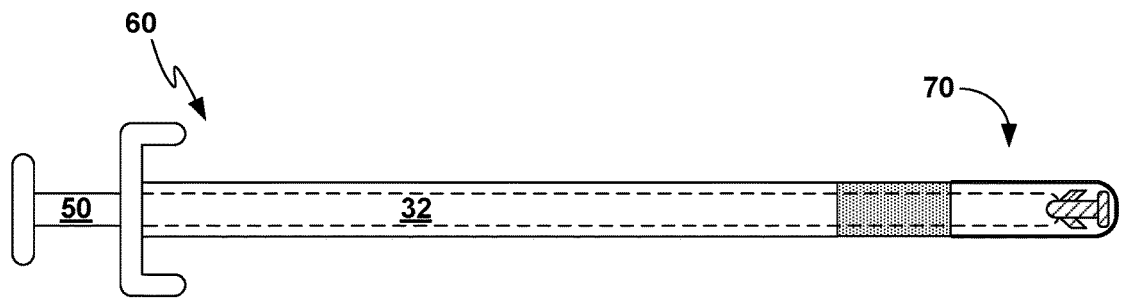
Figure 3C:
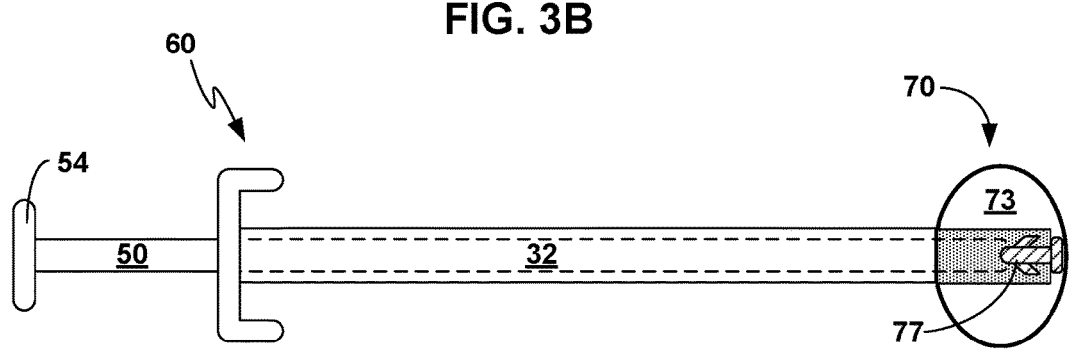

FIGS. 3A-3C illustrate an example system 60 including expandable valve element 70. Expandable valve element 70 is positionable within a bladder of a patient to facilitate selective excretion of urine from the patient's bladder. The system further includes insertion catheter 32 and insertion rod 50. Insertion catheter 32 and insertion rod 50 combine to facilitate insertion of expandable valve element 70 within a bladder of a patient via urinary tract of the patient when expandable valve element 70 is in a collapsed configuration, as shown in FIG. 3C. Insertion catheter 32 and insertion rod 50 may also facilitate retrieval of expandable valve element 70 from the bladder and/or urethra of the patient. Details and examples of insertion catheter 32 and insertion rod 50 were described with respect to FIGS. 1A-1C; for brevity, the details and examples of insertion catheter 32 and insertion rod 50 already described with respect to FIGS. 1A-1C are described in limited or no detail with respect to FIGS. 3A-3C.

Expandable valve element 70 is configured to assume an expanded configuration, as shown in FIG. 3B, to facilitate selective excretion of urine from a patient's bladder when positioned within the patient's bladder. Expandable valve element 70 configured to assume a collapsed configuration, as shown in FIG. 3C, to facilitate implantation to the patient's bladder through the patient's urethra. Expandable valve element 70 is configured to transition from the collapsed configuration to the expanded configuration after being positioned within the bladder of the patient via the urinary tract of the patient.

Expandable valve element 70 includes elastomeric outer element 72 and internal element 74 to facilitate the transition from the collapsed configuration to the expanded configuration. Elastomeric outer element 72 may be formed from a relatively soft polymer, such as silicone as a thin membrane configured to conform to the bladder wall in the trigone area.

Internal element 74 forms through-hole 75. One end of through-hole 75 is open and configured to receive distal end 58 of insertion rod 50. The other end of through-hole 75 is adjacent to an internal surface of elastomeric outer element 72. Snap-lock element 77 is secured to the internal surface of element 70 adjacent the other end of the through-hole. Expandable valve element 70 is configured to assume the collapsed position when in a relaxed state, as shown in FIG. 3B. Expandable valve element 70 is configured to assume the expanded configuration when snap-lock element 77 engages mating snap-lock features formed within through-hole 75 of internal element 74. For example, insertion rod 50 may be configured to engage snap-lock 77, and pull snap-lock 77 into through-hole 75 to engage mating snap-lock features formed within through-hole 75 while internal element 74 is held by insertion catheter 32. For example, internal element 74 may be held by way of a mechanical connection, such as a tether or clamp to insertion catheter 32 or by a magnetic connection to distal end 38 of insertion catheter 32. Similarly, insertion rod 50 may hold snap-lock 77 for pulling snap-lock 77 into through-hole 75 by way of a second mechanical connection, such as a tether or clamp to snap-lock 77.

When expandable valve element 70 is in the expanded configuration, elastomeric outer element 72 assumes a shape configured to facilitate sealing of the internal urethral opening of the patient when a ferromagnetic element of expandable valve element 70 is pulled toward the internal urethral opening of the patient by a magnet from outside the patient. In some examples, internal element 74 may include the ferromagnetic element of expandable valve element 70. When selectively controlled using the magnetic field to assume an open position, the expandable valve element is configured to allow urine to pass from the bladder of the patient, through the internal urethral opening of the patient and into the urethra of the patient.

In some examples, elastomeric outer element 72 may assume an about ellipsoid shape when in the expanded configuration. In the same or different examples, elastomeric outer element 72 may assumes the shape configured to facilitate sealing of the internal urethral opening of the patient while in a substantially relaxed state, such as that shown in FIG. 3A.

Figure 4:
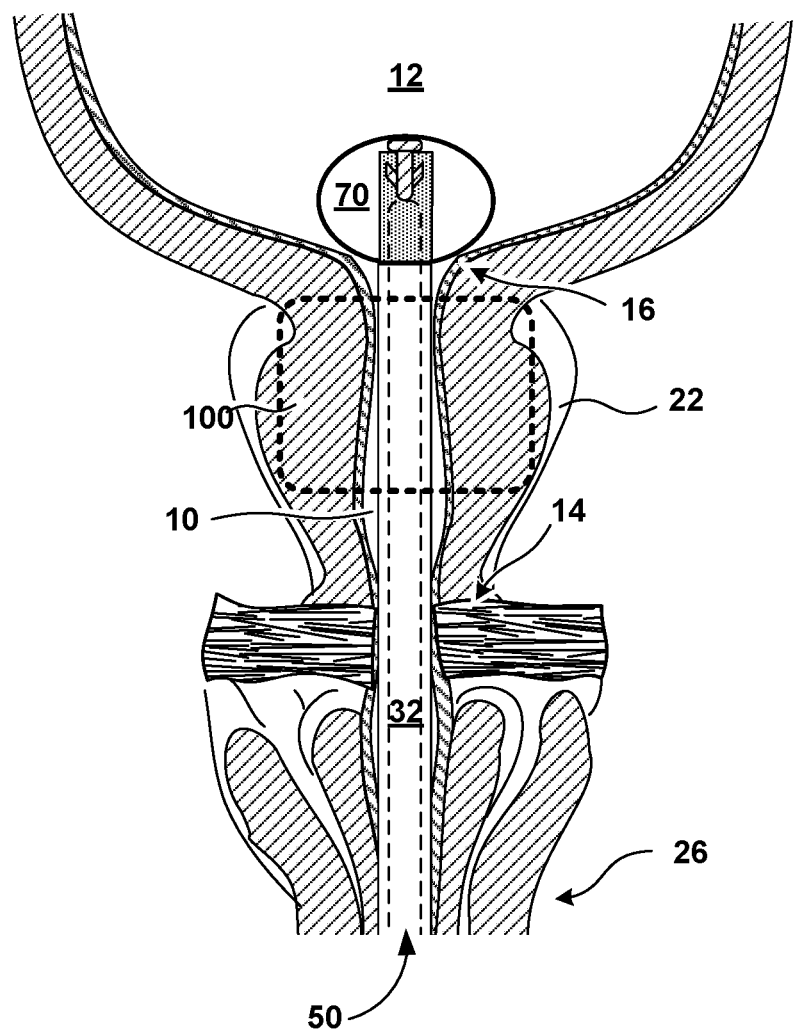
FIG. 4 illustrates the expandable valve element of FIGS. 3A-3C positioned within a bladder of a patient after insertion through the patient's urethra with the insertion catheter of FIGS. 3A-3C.

Expandable valve element 70 includes a ferromagnetic element, which may be included in internal element 74 that facilitates selective control of expandable valve element 70 using a magnet from outside a patient when the expandable valve element 70 is in the expanded configuration and positioned within the bladder of the patient. As illustrated in FIG. 4, when selectively controlled using the magnetic field to assume a closed position, expandable valve element 70 is configured to seal an internal urethral opening of the patient.

FIG. 4 represents a coronal cross section of anatomical structures surrounding urethra 10 of a male patient. FIG. 4 illustrates expandable valve element 70 in the expanded configuration and positioned within bladder 12 of a patient after insertion through urethra 10 with insertion catheter 32. Expandable valve element 70 is positioned within bladder 12 to control the flow of urine from bladder 12 into urethra 10. FIG. 4 further illustrates insertion catheter 32 and insertion rod 50 within urethra 10 following the insertion of expandable valve element 70 into bladder 12 via urethra 10.

In order to deliver expandable valve element 70 to bladder 12 via urethra 10, expandable valve element 70 is secured to distal end 38 of insertion catheter 32. Expandable valve element 70 is set into a collapsed configuration, according to the relaxed state of elastomeric outer element 72, as discussed with respect to FIGS. 3A-3C.

While secured to distal end 38 of insertion catheter 32 expandable valve element 70 is inserted into the end of urethra 10 and pushed through urethra 10 with insertion catheter 32 until reaching bladder 12. Once expandable valve element 70 reaches bladder 12, expandable valve element 70 assumes its expanded configuration. In one example, insertion rod 50 may be retracted, thereby pulling snap-lock element 77 until snap-lock element 77 engages mating snap-lock features formed within through-hole 75 of internal element 74. Once in the expanded configuration, expandable valve element 70 may block the urethra at the trigone area to prevent the discharge of urine within bladder into urethra 10.

Expandable valve element 70 includes a ferromagnetic material to facilitate its manipulation from a position external to the patient. In one example, magnetic device 100 may be worn in undergarments or outside of the pelvic floor. Device 10 can be configured to produce electromagnetic force when needed to pull expandable valve element 70 into position relative to bladder 12 to seal the bladder neck to prevent urine leak and/or repel expandable valve element 70 to release the temporary blockage of the bladder neck. Details of magnetic device 100 are discussed with respect to FIG. 2. For brevity, these details are not discussed with respect to FIG. 4.

Expandable valve element 70 may remain within bladder 12 for a prescribed period of time before being removed. When removal is needed, insertion catheter 32 will be inserted into urethra 10. In some examples, insertion catheter 32 may be configured to generate either permanent or activated magnetic field to attract expandable valve element 70 toward distal end 38 of insertion catheter 32. Insertion rod 50 can then be used to release snap-lock element 77 from mating snap-lock features formed within through-hole 75 of internal element 74. For example, insertion rod 50 may be used to press on snap-lock element 77 causing the snap lock features to release snap-lock element 77 from mating snap-lock features formed within through-hole 75 of internal element 74. Once insertion rod 50 is used to release snap-lock element 77 from mating snap-lock features formed within through-hole 75 of internal element 74, expandable valve element 70 assume the collapsed configuration. Once expandable valve element 70 is in the collapsed configuration, it may be extracted from the bladder via urethra 10 using insertion catheter 32. In some examples, expandable valve element 70 may be retracted into through-hole 36 of insertion catheter 32 in the collapsed configuration prior to its extraction via urethra 10.

Figure 5:
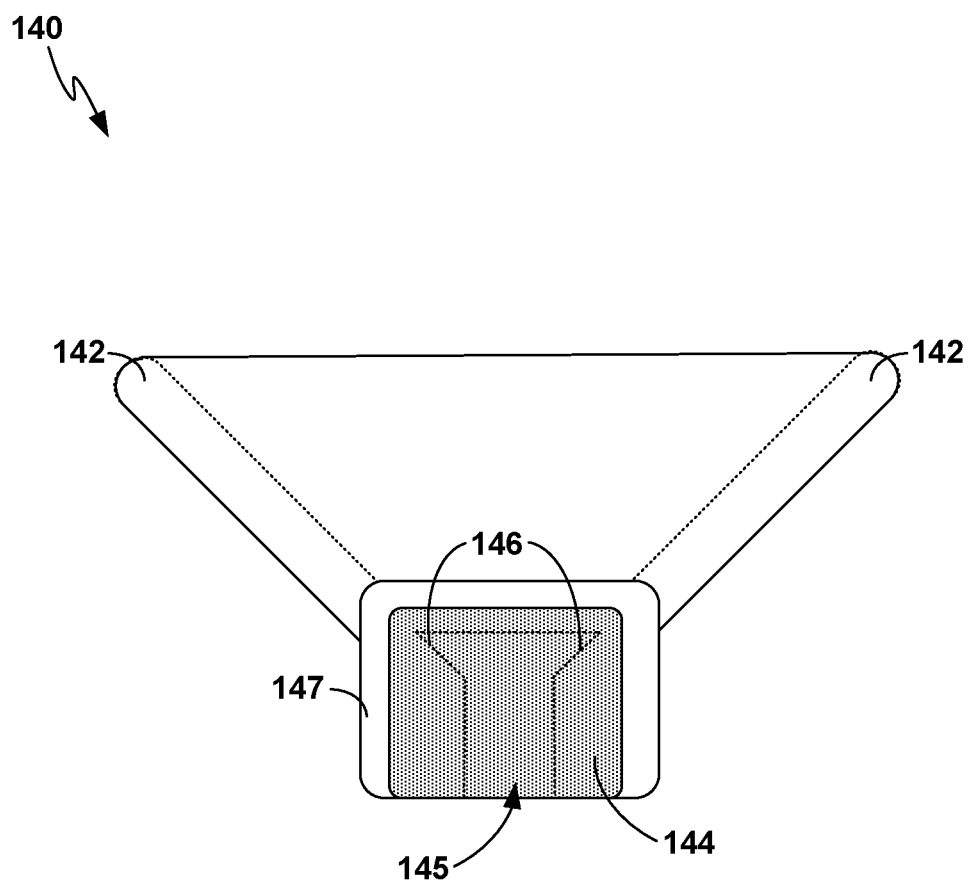
FIG. 5 illustrates an example cone-shaped expandable valve element that is positionable within a bladder of a patient to facilitate selective excretion of urine from the patient's bladder.

FIG. 5 illustrates a plan view of an example cone-shaped expandable valve element 140 that is positionable within a bladder of a patient to facilitate selective excretion of urine from the patient's bladder. Expandable valve element 140 includes elastomeric outer element 142. Elastomeric outer element 142 provides an approximate cone shape when in a relaxed state, as shown in FIG. 5. Elastomeric outer element 142 is configured to collapse within an insertion catheter to provide a collapsed configuration of expandable valve element 140.

Expandable valve element 140 further includes ferromagnetic element 144. As illustrated by FIG. 5, ferromagnetic element 144 is securely fixed to elastomeric outer element 142 in a position adjacent a center of the cone shape. In some examples, ferromagnetic element 144 is encapsulated with material 147 of elastomeric outer element 142.

Elastomeric outer element 142 is a thin membrane configured to substantially conform to the bladder wall in the trigone area. In some examples, elastomeric outer element 142 may be formed from a soft polymer, such as silicone.

Ferromagnetic element 144 forms recess 145, which includes a reverse taper providing beveled surface 146. As described in greater detail below, beveled surface 146 allows for controlled deployment and extraction of expandable valve element 140 from the bladder of a patient using a deployment tool.

When expandable valve element 140 is in the expanded configuration, elastomeric outer element 142 assumes the cone shape. The cone shape of elastomeric outer element 142 is configured to facilitate sealing of the internal urethral opening of the patient when ferromagnetic element 144 is pulled toward the internal urethral opening of the patient by the magnet from outside the patient.

Figure 6A:
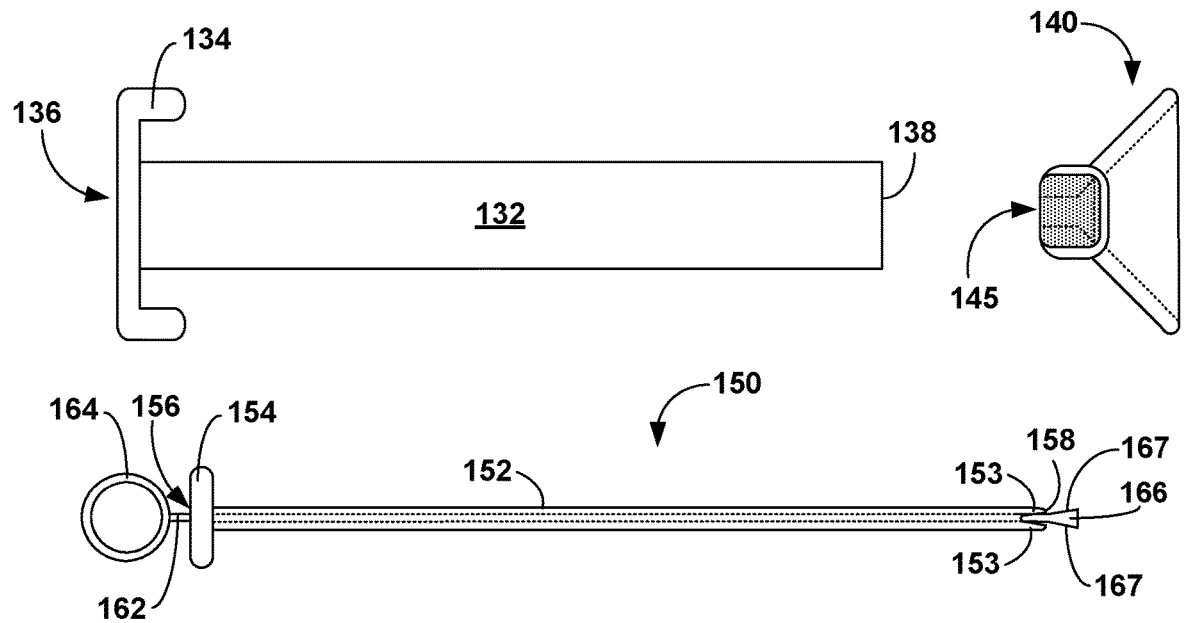
FIGS. 6A-6E illustrate a system including an example insertion catheter and the cone-shaped expandable valve element of FIG. 5.
Figure 6B:
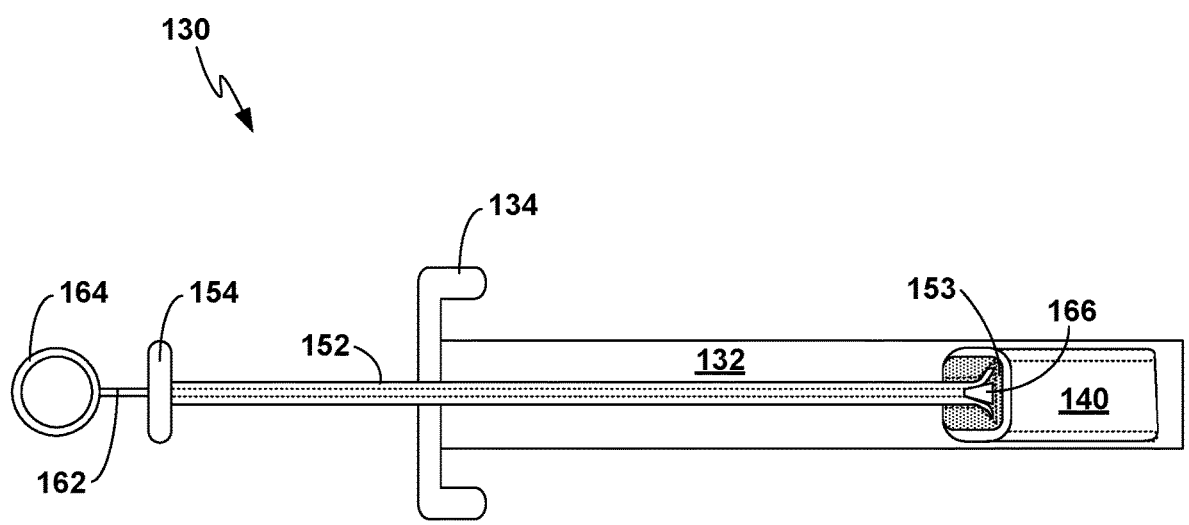
Figure 6C:
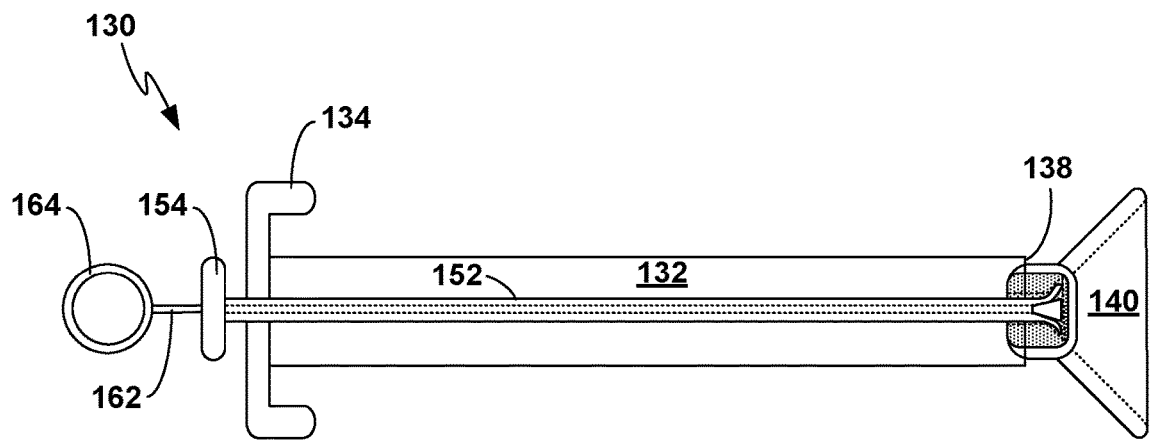

FIGS. 6A-6E illustrate a system 130 including insertion catheter 132, insertion tool 150 and cone-shaped expandable valve element 140. Expandable valve element 140 is positionable within a bladder of a patient to facilitate selective excretion of urine from the patient's bladder. Insertion catheter 132 and insertion tool 150 combine to facilitate insertion of expandable valve element 140 within a bladder of a patient via urinary tract of the patient when expandable valve element 140 is in a collapsed configuration, as shown in FIG. 6C. Insertion catheter 132 and insertion tool 150 may also facilitate retrieval of expandable valve element 140 from the bladder and/or urethra of the patient.

Expandable valve element 140 is configured to assume an expanded configuration, as shown in FIG. 6A, to facilitate selective excretion of urine from a patient's bladder when positioned within the patient's bladder. Expandable valve element 140 configured to assume a collapsed configuration, as shown in FIG. 6B, to facilitate implantation into the patient's bladder through the patient's urethra. Expandable valve element 140 is configured to transition from the collapsed configuration to the expanded configuration after being positioned within the bladder of the patient via the urinary tract of the patient.

Insertion catheter 132 and insertion tool 150 are configured to facilitate the implantation of the expandable valve element 140, while in the collapsed configuration, via the urinary tract of the patient and the remote deployment of expandable valve element 140 within the bladder of the patient. Expandable valve element 140 is configured to be inserted into distal end 138 of insertion catheter 132 for delivery to the bladder of a patient via the patient's urethra. Expandable valve element 140 assumes a folded and collapsed configuration within distal end 138 of insertion catheter 132, as shown in FIG. 6B.

Insertion tool 150 facilitates the delivery and recapture of expandable valve element 140 from distal end 138 of insertion catheter 132. As shown in FIG. 6A, insertion tool 132 includes an elongated tube section forming through-hole 136, which extends from a proximal end of insertion catheter 132 and adjacent grip 134 through distal end 138 of insertion catheter 132. Grip 134 eases hand-held manipulation (e.g., by a clinician) of insertion catheter 132 during an insertion or retrieval procedure.

Insertion tool 150 includes an elongated body element 152, which is configured to fit within through-hole 136 of insertion catheter 132. Insertion tool 150 includes grip 154 to facilitate hand-held manipulation (e.g., by a clinician) of insertion tool 150 during an insertion or retrieval procedure. Elongated body element 152 forms a through-hole 156. Wire element 162 extends within through-hole 156 from the proximal end of elongated body element 152 to distal end 158 of elongated body element 152.

Wire element 162 of insertion tool 150 includes wedge 166 with beveled surface 167. The proximal end of wire element 162 forms loop 164, which is configured to facilitate manipulation of wire element 162 relative to elongated body element 152. For example, a user may pull on loop 164 such that wedge 166 retracts into the distal end of through-hole 136, spreading petals 153 at distal end 158 of elongated body element 152. In one example, petals 153 may be formed from slits at distal end 158 of elongated body element 152.

Insertion tool 150 is longer than insertion catheter 132 such that the distal end 158 of insertion tool 150 may protrude from the distal end 138 of insertion catheter 132 when elongated body element 152 of insertion tool 150 is positioned within through-hole 136 of insertion catheter 132. This may help facilitate deployment and retrieval of expandable valve element 140 from distal end 138 of insertion catheter 132.

During an implantation procedure, expandable valve element 140 may be loaded into distal end 138 of insertion catheter 132 (FIG. 6B). Optionally, wire element 162 may be retracted such that petals 153 engage beveled surface 146 (FIG. 5) of expandable valve element 140. In some examples, expandable valve element 140 may come as part of a kit including insertion catheter 132 and insertion tool. In some such examples, expandable valve element 140 may be preloaded within distal end 138 of insertion catheter 132. Expandable valve element 140 is delivered to a patient's bladder via the urethra of the patient by inserting insertion catheter 132 into the urethra until distal end 138 of insertion catheter 132 is adjacent the bladder.

Once distal end 138 of insertion catheter 132 is adjacent the bladder, expandable valve element 140 may be deployed from the distal end 138 of insertion catheter 132. For example, a user, such as a clinician or the patient, may push on grip 154 of insertion tool to bring it closer to grip 134 of insertion catheter 132. This pushes expandable valve element 140 from distal end 138 of insertion catheter 132 (FIG. 6C).

Figure 6D:
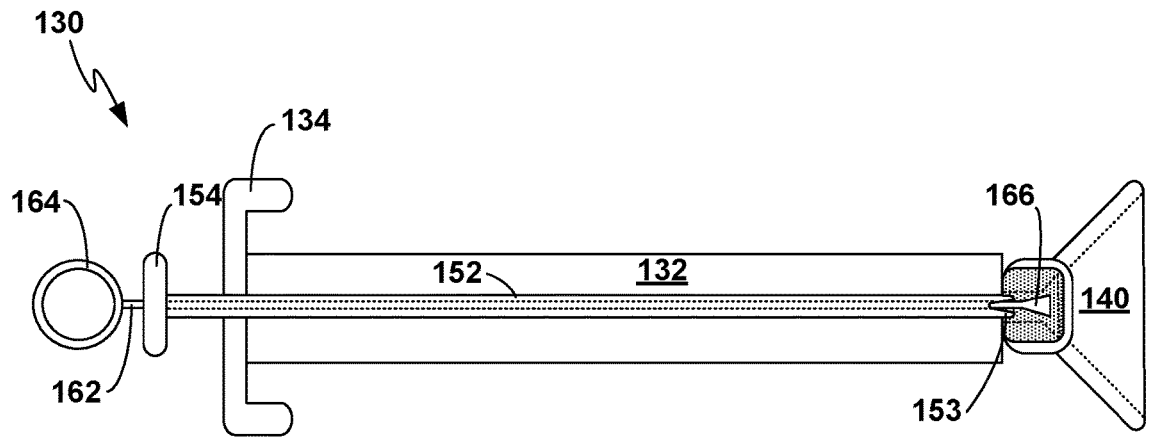
Figure 6E:
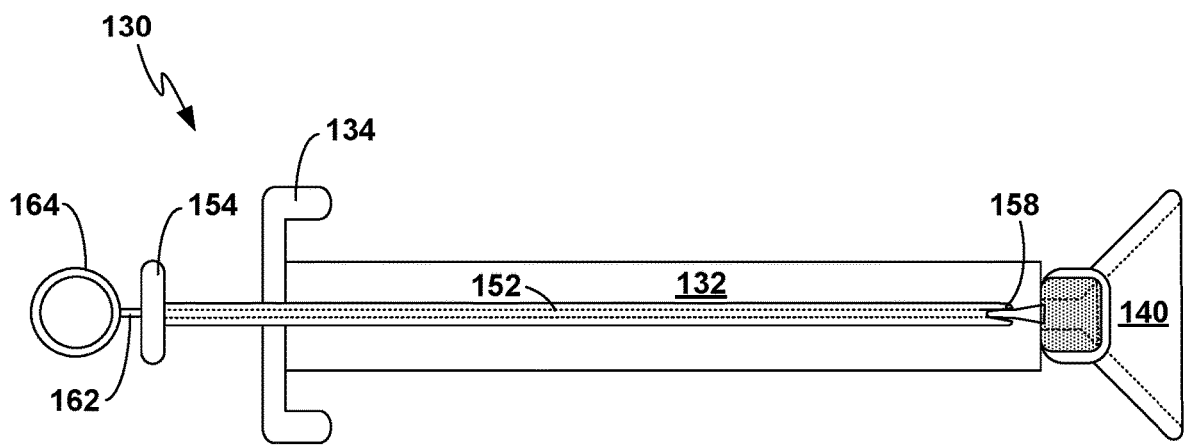

Once expandable valve element 140 is pushed from distal end 138 of insertion catheter 132, elastomeric outer element 142 of expandable valve element 140 assumes the approximate cone shape of in its relaxed state and expanded configuration. The user may then release expandable valve element 140 from the distal end of insertion tool 150 by pushing on loop 164 of wire element 162, bringing loop 164 closer to grip 154 of insertion tool 150. This causes wedge 166 to extend distally relative to elongated body element 152 such that petals 153 disengage beveled surface 146 of expandable valve element 140 (FIG. 6D). Once expandable valve element 140 is released from the distal end of insertion tool 150, insertion tool 150 may optionally be retracted into distal end 138 of insertion catheter 132 (FIG. 6E). The user may then retract insertion catheter 132 and insertion tool 150 from the urethra of the patient, leaving expandable valve element 140 within the bladder of the patient.

In other examples, an insertion tool may engage an expandable valve element to facilitate deployment and retrieval a patient's bladder from using any variety of techniques, including, but not limited to magnetic engagement, screw threads, a bayonet mount, other technique or a combination of such techniques. In another example, a lanyard or string may be attached to an expandable valve element and simply pulled to remove the expandable valve element, similar to tampon removal. Such a string/lanyard should be impregnated or coated with an effective antibacterial agent because the string may otherwise provide a pathway for bacteria into the sterile bladder compartment.

Insertion catheter 132 and insertion tool 150 may be formed from materials providing sufficient rigidity to facilitate insertion of expandable valve element 140 into a patient's urethra. For example, insertion catheter 132 may be formed from a polymeric material, or a metallic material, such as a stainless steel material, a combination thereof or another suitable material. Similarly, insertion tool 150 may be formed from a polymeric material, or a metallic material, such as a stainless steel material, a combination thereof or another suitable material.

When expandable valve element 140 is in the expanded configuration, elastomeric outer element 142 assumes the approximate cone shape configured to facilitate sealing of the internal urethral opening of the patient when a ferromagnetic element of expandable valve element 140 is pulled toward the internal urethral opening of the patient by a magnet from outside the patient and positioned to seal the internal urethral opening. In some examples, internal element 144 may include the ferromagnetic element of expandable valve element 140. When selectively controlled using the magnetic field to assume an open position, the expandable valve element is configured to allow urine to pass from the bladder of the patient, through the internal urethral opening of the patient and into the urethra of the patient.

In some examples, insertion catheter 132 also facilitates removal of expandable valve element 140 from the bladder of a patient. For example, expandable valve element 140 may be drawn to block the urethra at the trigone area by an external magnet. As one example, a user may insert insertion catheter 132 and insertion tool 150 into the urethra of the patient, and insertion tool 150 may be used to pull expandable valve element 140 into distal end 138 of insertion catheter 132. For example, the user may direct the distal end of insertion tool 150 into recess 145 of expandable valve element 140 (FIG. 6D). Then the user may pull on loop 164 of wire element to retract wedge 166 into elongated body element 152 such that petals 153 engage beveled surface 146 within recess 145 of expandable valve element 140 (FIG. 6C). Once petals 153 at the distal end of insertion tool 150 have engaged beveled surface 146 within recess 145 of expandable valve element 140, the user may pull on grip 154 to retract expandable valve element 140 into distal end 138 of insertion catheter 132 (FIG. 6B). When retracted into distal end 138 of insertion catheter 132 expandable valve element 140 assumes the collapsed configuration.

Figure 7:
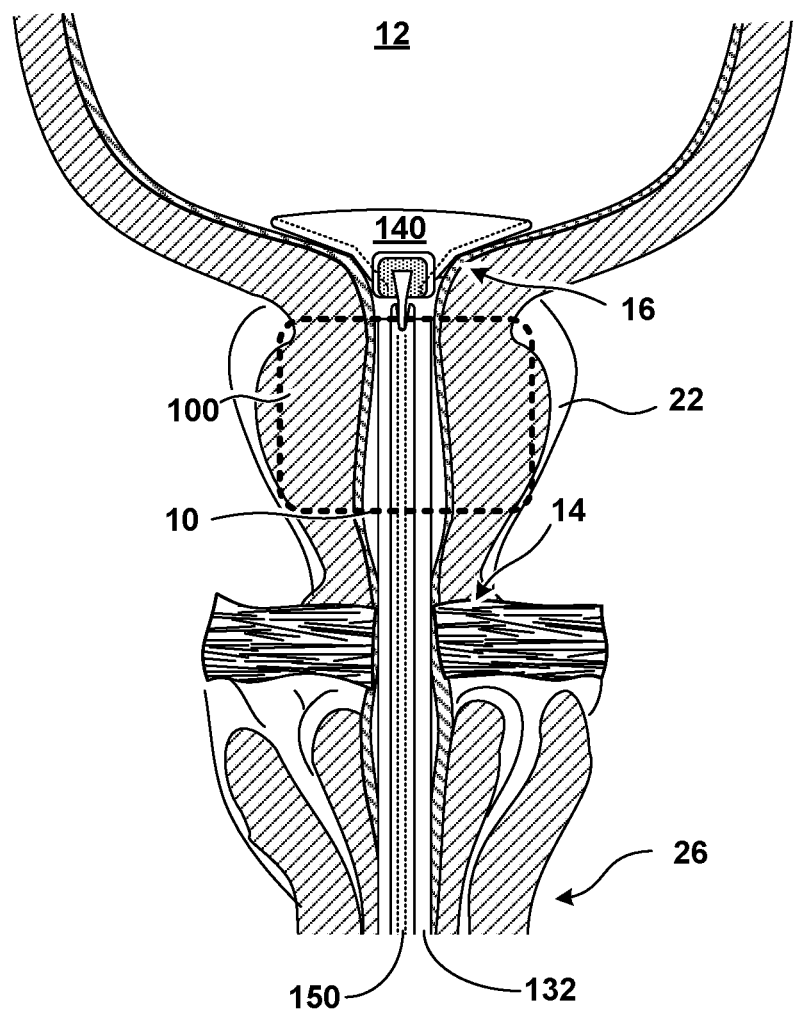
FIG. 7 illustrates the expandable valve element of FIG. 5 positioned within a bladder of a patient after insertion through the patient's urethra with the insertion catheter of FIGS. 6A-6E.

FIG. 7 illustrates the expandable valve element 140 of FIG. 5 positioned within a bladder of a patient after insertion through the patient's urethra with insertion catheter 132 and insertion tool 150. FIG. 7 represents a coronal cross section of anatomical structures surrounding urethra 10 of a male patient. FIG. 7 illustrates expandable valve element 140 in the expanded configuration and positioned within bladder 12 of a patient after insertion through urethra 10 with insertion catheter 132. Expandable valve element 140 is positioned within bladder 12 to control the flow of urine from bladder 12 into urethra 10. FIG. 7 further illustrates insertion catheter 132 and insertion tool 150 within urethra 10 following the insertion of expandable valve element 140 into bladder 12 via urethra 10.

As illustrated in FIG. 7, expandable valve element 140 is in its relaxed stated of an approximate cone shape to facilitate sealing of the internal urethral opening of the patient when a ferromagnetic element of expandable valve element 140 is pulled toward the internal urethral opening of the patient from outside the patient by magnet device 100.

Expandable valve element 140 includes a ferromagnetic material to facilitate its manipulation from a position external to the patient. In one example, magnetic device 100 may be worn in undergarments or outside of the pelvic floor, device 10 being configured to produce electromagnetic force when needed to pull expandable valve element 140 to seal the bladder neck to prevent urine leak and/or repel expandable valve element 140 to release the temporary blockage of the bladder neck. Details of magnetic device 100 are discussed with respect to FIG. 2. For brevity, these details are not discussed with respect to FIG. 7.

Figure 8:
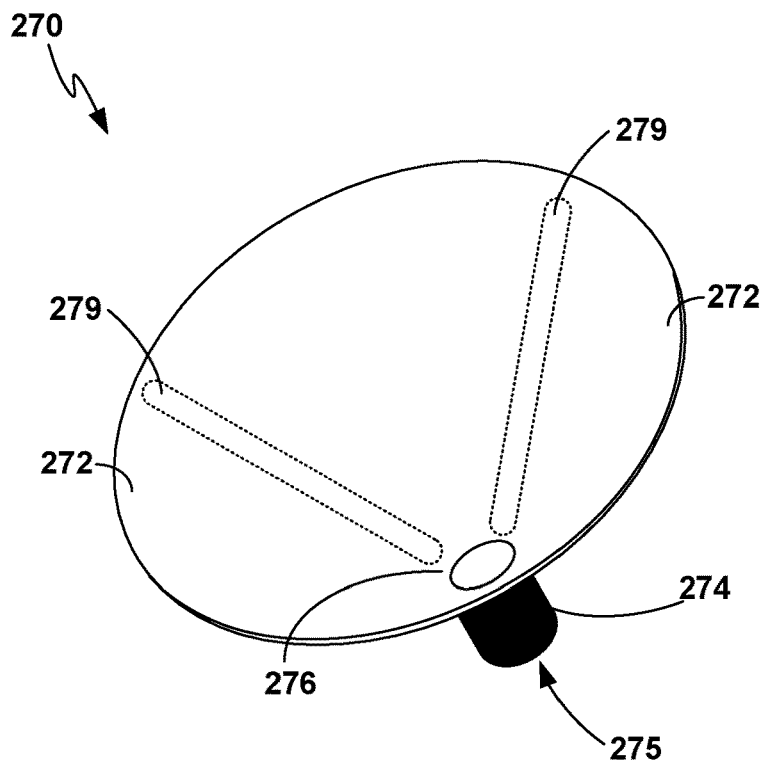
FIG. 8 illustrates another example of a cone-shaped expandable valve element configuration including buoyancy pockets.

FIG. 8 illustrates a perspective view of an example cone-shaped expandable valve element 270. Expandable valve element 270 is substantially similar to expandable valve element 140, except that expandable valve element 270 includes buoyancy pockets 279. For example, a user may deliver and retrieve expandable valve element 270 to a bladder of a patient via the urethra of the patient using insertion catheter 132 and insertion tool 150 as discussed with respect to expandable valve element 140. For brevity, such insertion and retrieval techniques are not repeated with respect to expandable valve element 270.

Like expandable valve element 140, expandable valve element 270 is positionable within a bladder of a patient to facilitate selective excretion of urine from the patient's bladder. Expandable valve element 270 includes elastomeric outer element 272. Elastomeric outer element 272 provides an approximate cone shape when in a relaxed state, as shown in FIG. 8. Elastomeric outer element 272 is configured to collapse within an insertion catheter to provide a collapsed configuration of expandable valve element 270.

Expandable valve element 270 further includes ferromagnetic element 274. As illustrated by FIG. 8, ferromagnetic element 274 is securely fixed to elastomeric outer element 272 in a position adjacent a center of the cone shape. In some examples, ferromagnetic element 274 is encapsulated with material of elastomeric outer element 272.

Ferromagnetic element 274 forms recess 275, which includes beveled surface (not shown in FIG. 8). The beveled surface allows for controlled deployment and extraction of expandable valve element 270 from the bladder of a patient using a deployment tool.

When expandable valve element 270 is in the expanded configuration, elastomeric outer element 272 assumes the cone shape. The cone shape of elastomeric outer element 272 is configured to facilitate sealing of the internal urethral opening of the patient when ferromagnetic element 274 is pulled toward the internal urethral opening of the patient by the magnet from outside the patient.

Buoyancy pockets 279 are located within elastomeric outer element 273. Buoyancy pockets 279 reduce the average density of expandable valve element 270. For example, buoyancy pockets 279 may be used to provide a desired buoyancy for expandable valve element 270, such as an approximately neutral buoyancy within the bladder of a patient. In addition, buoyancy pockets 279 combine with ferromagnetic element 274 to bias the orientation of expandable valve element 270 in the absence of an external electromagnetic force being applied to ferromagnetic element 274 such that the center 276 of the cone shape faces in a downward direction due to gravity. The may help direct center 276 of the cone shape into the trigone area of the patient in order to more consistently seal the internal urethral opening of the bladder of the patient.

Figure 9:
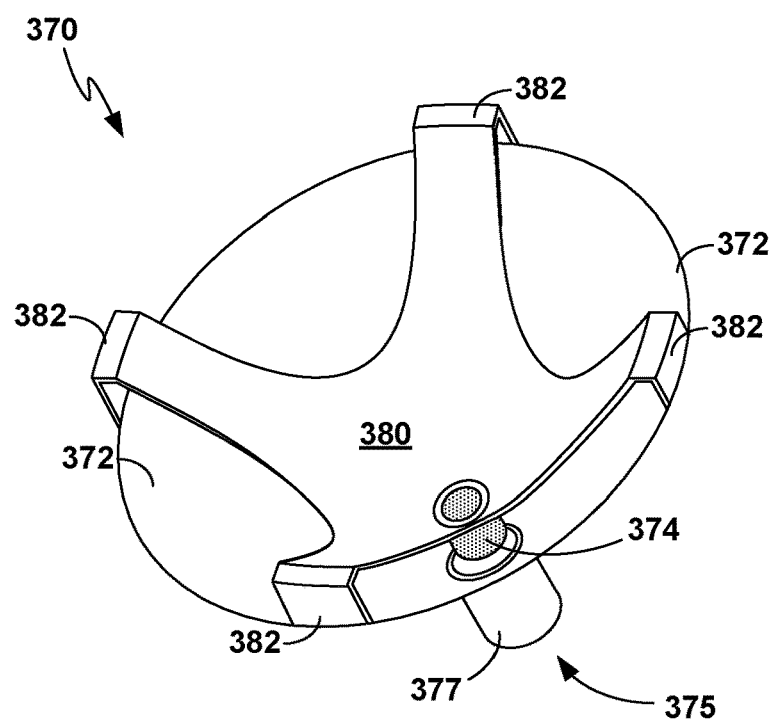
FIG. 9 illustrates an alternative cone-shaped expandable valve element configuration including an inner element flexibly secured to an elastomeric outer element.

FIG. 9 illustrates another example of a cone-shaped expandable valve element 370. Expandable valve element 370 includes inner element 380 flexibly secured to elastomeric outer element 372. Elastomeric outer element 372 and inner element 380 are configured to collapse within an insertion catheter to provide a collapsed configuration of expandable valve element 370. In this manner, expandable valve element 370 is similar to expandable valve element 140. For example, a user may deliver and retrieve expandable valve element 370 to a bladder of a patient via the urethra of the patient using insertion catheter 132 and insertion tool 150 as discussed with respect to expandable valve element 140. For brevity, such insertion and retrieval techniques are not repeated with respect to expandable valve element 370.

Like expandable valve element 140, expandable valve element 370 is positionable within a bladder of a patient to facilitate selective excretion of urine from the patient's bladder. Expandable valve element 370 includes elastomeric outer element 372 with annular tubular portion 377 forming through-hole 375. Elastomeric outer element 372 provides an approximate cone shape when in a relaxed state, as shown in FIG. 9. Annular tubular portion 377 is configured to extend into the urethra of a patient at the trigone area such that hole 375 at the center of the cone shape is coincident with the internal urethral opening of the patient. For example, annular tubular portion 377 may be configured to extend within the urethra of the patient when expandable valve element 370 is positioned within the bladder of the patient. Elastomeric outer element 372 is a thin membrane configured to conform to the bladder wall in the trigone area. In some examples, elastomeric outer element 372 may be formed from a soft polymer, such as silicone.

Inner element 380 is connected to elastomeric outer element 372 via supports 382 at the outer perimeter of elastomeric outer element 372. Inner element 380 includes ferromagnetic element 374. Inner element 380 is flexibly secured to elastomeric outer element 372 such that elastomeric inner element 380 selectively seals hole 375 when ferromagnetic element 374 is pulled toward the internal urethral opening of the patient by a magnet from outside the patient. Inner element 380 may also be a thin membrane. In some examples, inner element 380 may be formed from a soft polymer, such as silicone.

Figure 10:
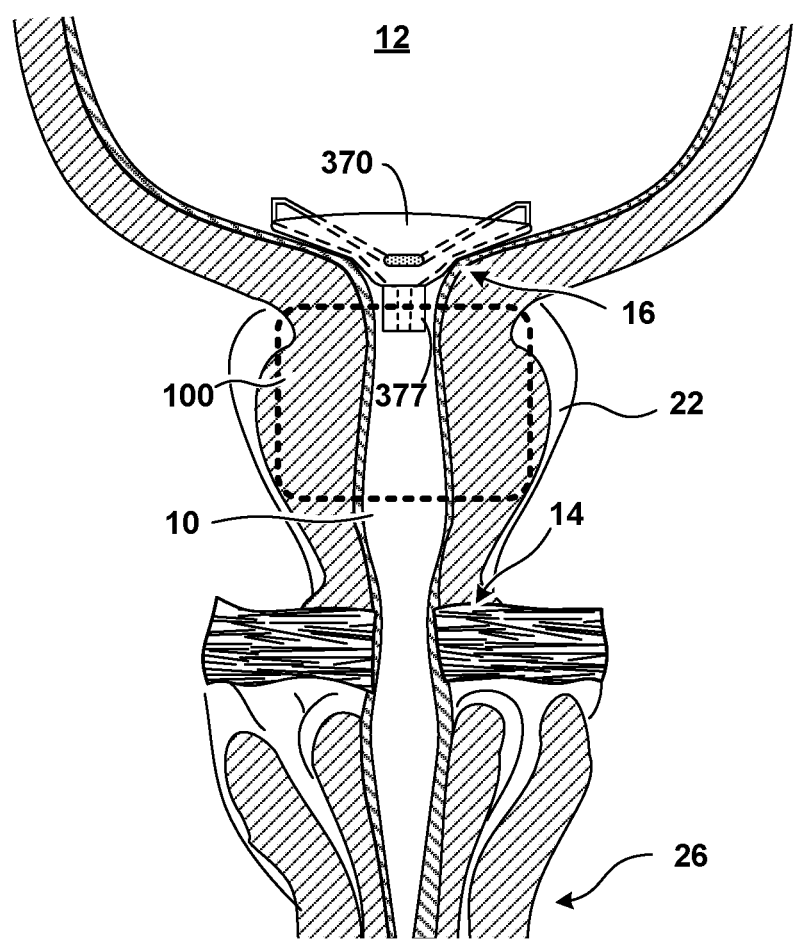
FIG. 10 illustrates the expandable valve element of FIG. 9 positioned within a bladder of a patient after insertion through the patient's urethra with the insertion catheter of FIGS. 6A-6E.

FIG. 10 illustrates the expandable valve element of FIG. 9 positioned within a bladder of a patient after insertion through the patient's urethra with insertion catheter 132 and insertion tool 150. FIG. 10 represents a coronal cross section of anatomical structures surrounding urethra 10 of a male patient. FIG. 10 illustrates expandable valve element 370 in the expanded configuration and positioned within bladder 12 of a patient after insertion through urethra 10 with insertion catheter 132. Expandable valve element 370 is positioned within bladder 12 to control the flow of urine from bladder 12 into urethra 10.

In FIG. 10, expandable valve element 370 is in its relaxed stated to form an approximate cone shape to facilitate sealing of the internal urethral opening of the patient. In particular, expandable valve element 370 seals the internal urethral opening of the patient when ferromagnetic element 374 of elastomeric inner element 380 is pulled toward the internal urethral opening of the patient by magnet device 100 from outside the patient to seal hole 375 in annular tubular portion 377.

Ferromagnetic element 374 of elastomeric inner element 380 facilitates manipulation of expandable valve element 370 from a position external to the patient. In one example, magnetic device 100 may be worn in undergarments or outside of the pelvic floor, device 10 being configured to produce electromagnetic force when needed to pull ferromagnetic element 374 of elastomeric inner element 380 towards hole 375, to seal hole 375, and, therefore, the internal urethral opening to prevent urine leak and/or repel ferromagnetic element 374 of elastomeric inner element 380 to release the temporary blockage of the internal urethral opening. Details of magnetic device 100 are discussed with respect to FIG. 2. For brevity, these details are not discussed with respect to FIG. 10.

Figure 11:
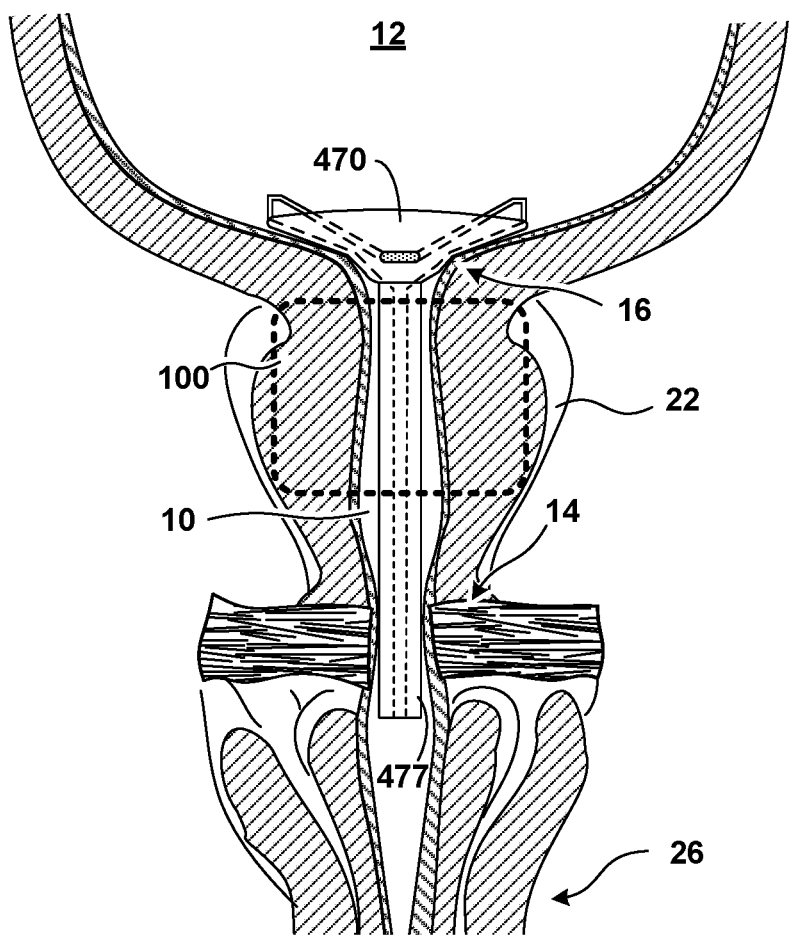
FIG. 11 illustrates another example configuration of an expandable valve element, the configuration including an annular tubular portion extending beyond an external urinary sphincter of the patient within a bladder of a patient after insertion through the patient's urethra with the insertion catheter of FIGS. 6A-6E.

FIG. 11 illustrates an example expandable valve element 470 positioned within a bladder of a patient after insertion through the patient's urethra with insertion catheter 132 and insertion tool 150. FIG. 11 represents a coronal cross section of anatomical structures surrounding urethra 10 of a male patient. FIG. 11 illustrates expandable valve element 470 in the expanded configuration and positioned within bladder 12 of a patient after insertion through urethra 10 with insertion catheter 132. Expandable valve element 470 is positioned within bladder 12 to control the flow of urine from bladder 12 into urethra 10.

As illustrated in FIG. 11, expandable valve element 470 is in its relaxed stated of an approximate cone shape to facilitate sealing of the internal urethral opening of the patient. In particular, expandable valve element 470 seals the internal urethral opening of the patient when a ferromagnetic element of its elastomeric inner element is pulled toward the internal urethral opening of the patient by magnet device 100 from outside the patient to seal a hole in annular tubular portion 477.

Expandable valve element 470 is substantially similar to expandable valve element 370 except that annular tubular portion 477 extends beyond external urinary sphincter 14 when the cone shape of expandable valve element 470 is within bladder 12. Annular tubular portion 477 is configured to maintain a flow passage within the urethra from the hole at the center of the cone shape to a position within the urethra beyond the external urinary sphincter. Because annular tubular portion 477 is configured to maintain a flow passage within the urethra from the hole at the center of the cone shape to a position within the urethra beyond the external urinary sphincter, expandable valve element 470 may be used to manage urinary retention in addition to urinary incontinence. In this manner, expandable valve element 470 may provide an alternative to external catheters used to manage urinary incontinence. Because expandable valve element 470 may remain in the patient for a determined period of time, whereas external catheters may only be used once, expandable valve element 470 may reduce the risk of bladder infections for a patient caused by inserting a device, such as a catheter, into the sterile environment of a bladder in order to manage urinary incontinence.

Figure 12:
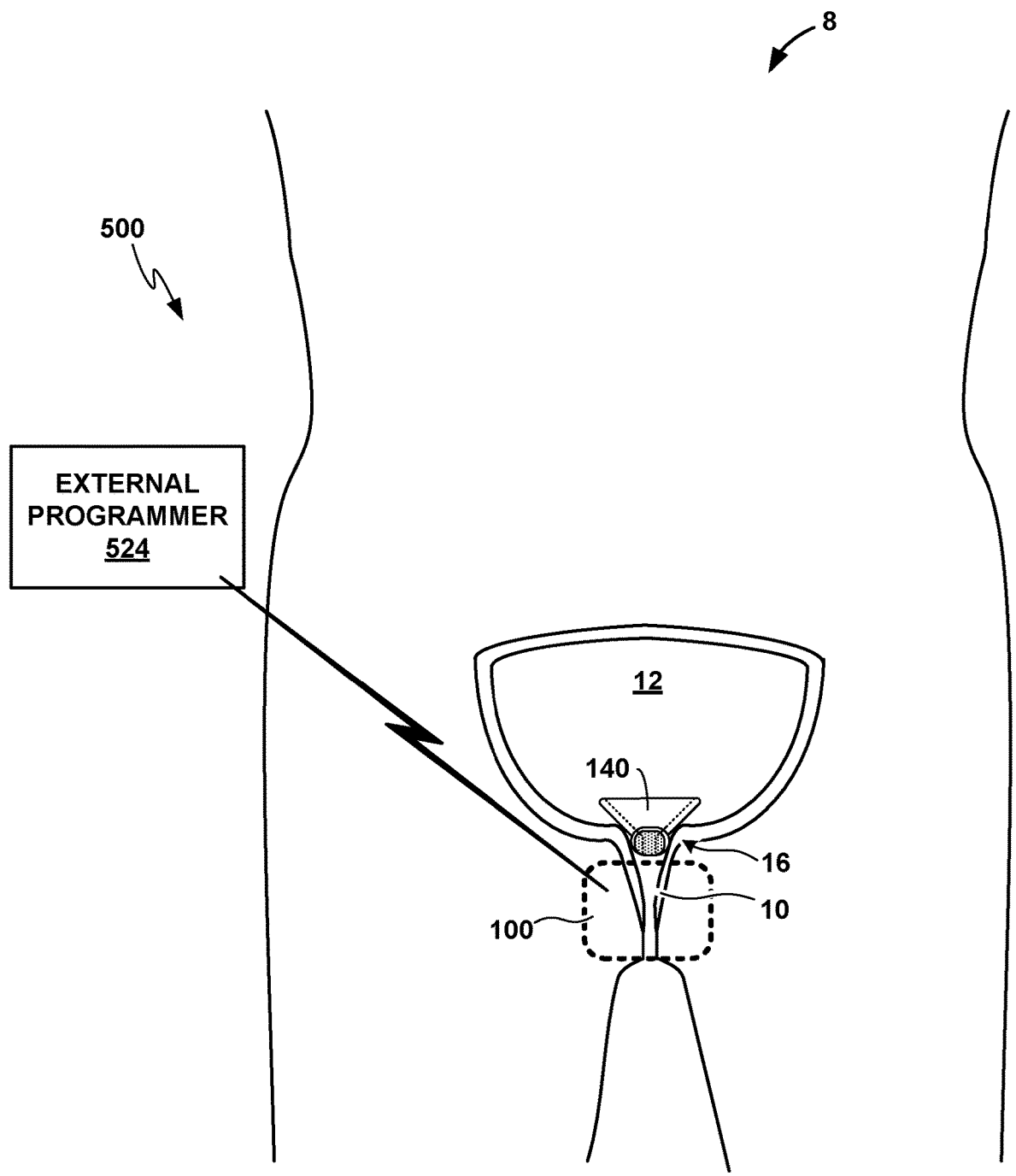
FIG. 12 is a conceptual diagram illustrating an example of a therapy system including a programmer, an external magnet and an expandable valve element that is positionable within a bladder of a patient to facilitate selective excretion of urine from the patient's bladder to a patient to manage a bladder dysfunction, such as urinary retention, an overactive bladder, urgency, or urinary incontinence.

FIG. 12 is a conceptual diagram illustrating example therapy system 500 for managing a bladder dysfunction of patient 8. Therapy system 500 includes medical device programmer 524, magnet device 100 and expandable valve element 140. As previously mentioned, expandable valve element 140 is positionable within bladder 12 of patient 8 to facilitate selective excretion of urine from the patient's bladder to a patient to manage a bladder dysfunction, such as urinary retention, an overactive bladder, urgency, or urinary incontinence. In other example therapy systems, different expandable valve element 140 may be used to facilitate selective excretion of urine from the patient's bladder, including, but not limited to expandable valve element 40, expandable valve element 70, expandable valve element 370, expandable valve element 470 or other expandable valve element.

As discussed above, magnetic device 100 may be worn in undergarments or outside of the pelvic floor to produce electromagnetic force when needed to pull expandable valve element 140 to seal bladder 12 adjacent internal urinary sphincter 16 to prevent urine leak and/or repel expandable valve element 140 to release the temporary blockage of the bladder neck.

External programmer 524 communicates with magnet device 100 via a wireless communication protocol. Magnet device 100 and programmer 524 may communicate via wireless communication using any techniques known in the art. Examples of communication techniques may include, for example, low frequency or radiofrequency (RF) telemetry, but other techniques are also contemplated.

In some examples, programmer 524 may be a wearable communication device, such as a key fob or a wristwatch, handheld computing device, computer workstation, or networked computing device. Programmer 524 may include a user interface that receives input from a user (e.g., patient 8, a patient caretaker or a clinician). In some examples, the user interface includes, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 524 can additionally or alternatively include a peripheral pointing device, such as a mouse, via which a user may interact with the user interface. In some examples, a display of programmer 524 may include a touch screen display, and a user may interact with programmer 524 via the display. It should be noted that the user might also interact with programmer 524 and/or magnet device 100 remotely via a networked computing device.

Programmer 524 allows a user, such as patient 8, to selectively control expandable valve element 140 via magnet device 100 from outside the patient. As one example, the user may enter an input into programmer 524 to instruct magnet device 100 to generate a magnetic field configured to repel a ferromagnetic element in expandable valve element 140 such that expandable valve element 140 assumes an open position to allow urine to pass from bladder 12 patient 8. Programmer 524 also allows the user, such as patient 8, to selectively unseal the internal urethral opening of the patient by changing a current applied to the electromagnet of magnet device 100.

In some examples, programmer 524, may be used to selectively titrate the magnetic field strength, such that the downward force on bladder neck can be adjusted. Such configurability may provide increased efficacy as well as improved patient comfort by customizing the magnetic forces to the needs of a patient.

In the same or different examples, programmer 524 and/or magnet device 100 may to prevent prolonged valve closure, which can lead to high bladder pressure and renal reflux, the system has a safety time-out feature. After a certain period of time, programmer 524 and/or magnet device 100 may present an alert to the user to remove or turn off magnet device 100. Alternatively, magnet device 100 may be disabled automatically after a certain period of time. An example for time out duration would be 3 hours, although a user may specify a different time-out period using programmer 524.

In the same or different examples, programmer 524 and/or magnet device 100 may store a record of the activation of magnet device 100, which may be useful in evaluating the patient's bladder dysfunction and usefulness of system 500 including expandable valve element 140. Such a record may be retrieved by a user of programmer 524 or remotely via another computing device.

The techniques described in this disclosure may be implemented, at least in part, in hardware, software, firmware, or any combination thereof. For example, various aspects of the described techniques, including the disclosed techniques relating to magnet devices and programmers, may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "control system," "controller" or "control module" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various techniques described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware, firmware, or software components. Rather, functionality associated with one or more modules or units may be performed by separate hardware, firmware, or software components, or integrated within common or separate hardware, firmware, or software components.

The techniques described in this disclosure may also be embodied or encoded in a computer-readable medium, such as a transitory or non-transitory computer-readable storage medium, containing instructions. Instructions embedded or encoded in a computer-readable medium, including a computer-readable storage medium, may cause one or more programmable processors, or other processors, such one or more processors included in a control system, to implement one or more of the techniques described herein, such as when instructions included or encoded in the computer-readable medium are executed by the one or more processors. Non-transitory computer-readable storage media may include random access memory (RAM), read only memory (ROM), programmable read only memory (PROM), erasable programmable read only memory (EPROM), electronically erasable programmable read only memory (EE- PROM), flash memory, a hard disk, a compact disc ROM (CD-ROM), a floppy disk, a cassette, magnetic media, optical media, or other computer-readable media. In some examples, an article of manufacture may comprise one or more computer-readable storage media.

Various examples of this disclosure have been described. These and other examples are within the scope of the following claims.

What is claimed is:

1. A device comprising:
an expandable valve element configured to be positioned within a bladder of a patient via a urinary tract of the patient when the expandable valve element is in a collapsed configuration,
wherein the expandable valve element is configured to transition from the collapsed configuration to an expanded configuration after being positioned within the bladder of the patient via the urinary tract of the patient,
wherein the expandable valve element includes a ferromagnetic element that facilitates selective control of the expandable valve element with a magnetic field between an open position and a closed position when positioned within the bladder of the patient,
wherein, in the closed position and in the expanded configuration, the expandable valve element is configured to seal an internal urethral opening of the patient,
wherein, in the open position, the expandable valve element is configured to allow urine to pass from the bladder of the patient, through an internal urethral opening of the patient and into a urethra of the patient,
wherein the expandable valve element comprises an elastomeric outer element and a through-hole, and
wherein the expandable valve element is configured to assume the collapsed configuration when an insertion rod is introduced through the through-hole and a distal end of the insertion rod is pressed against an internal surface of the elastomeric element to stretch the elastomeric outer element such that the elastomeric outer element assumes an elongated shape.

2. The device of claim 1, wherein the expandable valve element comprises an internal element forming the through-hole, one end of the through-hole being open and the other end of the through-hole being adjacent to the internal surface of the elastomeric element; and
wherein, when the expandable valve element is in the expanded configuration, the elastomeric outer element assumes a shape configured to facilitate sealing of the internal urethral opening of the patient when the ferromagnetic element is pulled toward the internal urethral opening of the patient by the magnetic field.

3. The device of claim 2, wherein the internal element includes the ferromagnetic element.

4. The device of claim 2, wherein the elastomeric outer element assumes the shape configured to facilitate sealing of the internal urethral opening of the patient while in a substantially relaxed state.

5. The device of claim 2, wherein the elastomeric outer element provides an about ellipsoid shape when in the expanded configuration.

6. The device of claim 2, wherein the internal element is configured to be more rigid than the elastomeric outer element.

7. The device of claim 1, wherein the elastomeric outer element is configured to conform to a bladder wall in a trigone area of the patient.

8. A system comprising:
an external magnet configured to produce a magnetic field; and
an implantable device, the implantable device comprising an expandable valve element configured to be positioned within a bladder of a patient via a urinary tract of the patient when the expandable valve element is in a collapsed configuration,
wherein the expandable valve element is configured to transition from the collapsed configuration to an expanded configuration after being positioned within the bladder of the patient via the urinary tract of the patient,
wherein the expandable valve element includes a ferromagnetic element that facilitates selective control of the expandable valve element with the magnetic field between an open position and a closed position when positioned within the bladder of the patient,
wherein, in the closed position and in the expanded configuration, the expandable valve element is configured to seal an internal urethral opening of the patient,
wherein, in the open position, the expandable valve element is configured to allow urine to pass from the bladder of the patient, through an internal urethral opening of the patient and into a urethra of the patient,
wherein the expandable valve element comprises an elastomeric outer element and a through-hole, and
wherein the expandable valve element is configured to assume the collapsed configuration when an insertion rod is introduced through the through-hole and a distal end of the insertion rod is pressed against an internal surface of the elastomeric element to stretch the elastomeric outer element such that the elastomeric outer element assumes an elongated shape.

9. The system of claim 8, wherein the expandable valve element comprises an internal element forming the through-hole, one end of the through-hole being open and the other end of the through-hole being adjacent to an internal surface of the elastomeric element; and
wherein, when the expandable valve element is in the expanded configuration, the elastomeric outer element assumes a shape configured to facilitate sealing of the internal urethral opening of the patient when the ferromagnetic element is pulled toward the internal urethral opening of the patient by the magnetic field.

10. The system of claim 9, wherein the internal element includes the ferromagnetic element.

11. The system of claim 9, wherein the elastomeric outer element assumes the shape configured to facilitate sealing of the internal urethral opening of the patient while in a substantially relaxed state.

12. The system of claim 9, wherein the elastomeric outer element provides an about ellipsoid shape when in the expanded configuration.

13. The system of claim 9, wherein the internal element is configured to be more rigid than the elastomeric outer element.

14. The system of claim 8, wherein the elastomeric outer element is configured to conform to a bladder wall in a trigone area of the patient.

15. A method comprising:
inputting a control signal to vacate urine from a user's bladder of a patient via a programmer of a urinary tract valve system,
wherein the urinary tract valve system comprises:
the programmer;
a wearable magnet device that includes an electromagnet; and an implantable device in the patient, the implantable device comprising an expandable valve element configured to be positioned within the bladder of the patient via a urinary tract of the patient when the expandable valve element is in a collapsed configuration, wherein the expandable valve element is configured to transition from the collapsed configuration to an expanded configuration after being positioned within the bladder of the patient via the urinary tract of the patient, wherein the expandable valve element includes a ferromagnetic element that facilitates selective control of the expandable valve element with a magnetic field between an open position and a closed position when positioned within the bladder of the patient, wherein, in the closed position and in the expanded configuration, the expandable valve element is configured to seal an internal urethral opening of the patient, wherein, in the open position, the expandable valve element is configured to allow urine to pass from the bladder of the patient, through an internal urethral opening of the patient and into a urethra of the patient, wherein the expandable valve value element comprises an elastomeric outer element and a through-hole, and wherein the expandable valve element is configured to assume the collapsed configuration when an insertion rod is introduced through the through-hole and a distal end of the insertion rod is pressed against an internal surface of the elastomeric element to stretch the elastomeric outer element such that the elastomeric outer element assumes an elongated shape.

16. The method of claim 15, wherein the expandable valve element comprises an internal element forming the through-hole, one end of the through-hole being open and the other end of the through-hole being adjacent to the internal surface of the elastomeric element; and wherein, when the expandable valve element is in the expanded configuration, the elastomeric outer element assumes a shape configured to facilitate sealing of the internal urethral opening of the patient when the ferromagnetic element is pulled toward the internal urethral opening of the patient by the magnetic field.

17. The method of claim 16, wherein the internal element includes the ferromagnetic element.

18. The method of claim 16, wherein the elastomeric outer element assumes the shape configured to facilitate sealing of the internal urethral opening of the patient while in a substantially relaxed state.

19. The method of claim 16, wherein the elastomeric outer element provides an about ellipsoid shape when in the expanded configuration.

20. The method of claim 16, wherein the internal element is configured to be more rigid than the elastomeric outer element.

* * * * *